United States Patent
Garrity

[19]

[11] Patent Number: 6,150,656
[45] Date of Patent: Nov. 21, 2000

[54] METHOD OF ASSEMBLY AND INSPECTION FOR A GAS TURBINE ENGINE

[75] Inventor: Michael P. Garrity, Worcester, Mass.

[73] Assignee: United Technologies Corporation, Hartford, Conn.

[21] Appl. No.: 09/208,642

[22] Filed: Dec. 10, 1998

[51] Int. Cl.[7] ...................................................... G01M 11/00
[52] U.S. Cl. .................... 250/302; 250/459.1; 250/461.1
[58] Field of Search ................................ 250/302, 461.1, 250/459.1; 382/141, 152

[56] References Cited

U.S. PATENT DOCUMENTS

| | | |
|---|---|---|
| 2,382,355 | 8/1945 | Warren . |
| 2,410,277 | 10/1946 | Farris . |
| 2,761,069 | 8/1956 | Brayer . |
| 2,939,271 | 6/1960 | Nadel . |
| 4,670,298 | 6/1987 | Lucas et al. . |
| 4,780,925 | 11/1988 | Sherman . |
| 4,804,806 | 2/1989 | Orr, Jr. et al. . |
| 4,918,980 | 4/1990 | Theofanous . |
| 4,928,212 | 5/1990 | Benavides . |
| 4,963,752 | 10/1990 | Landis et al. ........................ 250/459.1 |
| 5,053,930 | 10/1991 | Benavides . |
| 5,149,453 | 9/1992 | Parekh . |
| 5,197,288 | 3/1993 | Newland et al. . |
| 5,270,116 | 12/1993 | Melancon et al. . |
| 5,286,922 | 2/1994 | Curtiss . |
| 5,451,343 | 9/1995 | Neckers et al. . |
| 5,531,105 | 7/1996 | Leong et al. . |
| 5,567,051 | 10/1996 | Annati et al. . |
| 5,605,730 | 2/1997 | Treleaven . |
| 5,605,738 | 2/1997 | McGinness et al. . |
| 5,666,725 | 9/1997 | Ward . |
| 5,667,840 | 9/1997 | Tingey et al. . |
| 5,773,790 | 6/1998 | Moore et al. . |

*Primary Examiner*—Constantine Hannaher

[57] ABSTRACT

A method of locating a component requiring a supplemental restraining device on a portion of a gas turbine engine includes applying a fluorescent material to the component, and irradiating the component and surrounding components on the portion of the gas turbine engine with electromagnetic radiation that causes the fluorescent material to emit visible light and thereby increase the visibility of the component. The method may be used to install and/or inspect a lock-wire that in the presence of the electromagnetic radiation has a visibly contrasting appearance compared to that of the component requiring a lock-wire.

20 Claims, 2 Drawing Sheets

FIG.1
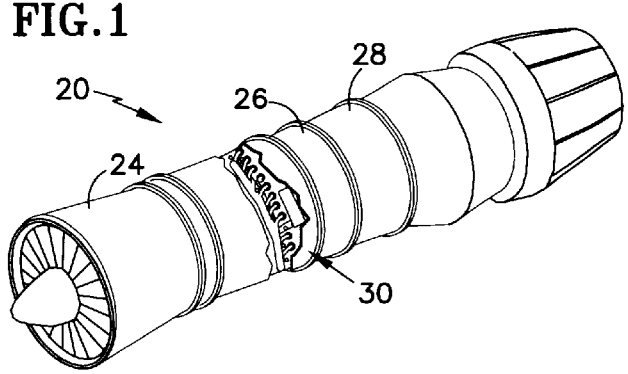
FIG.2
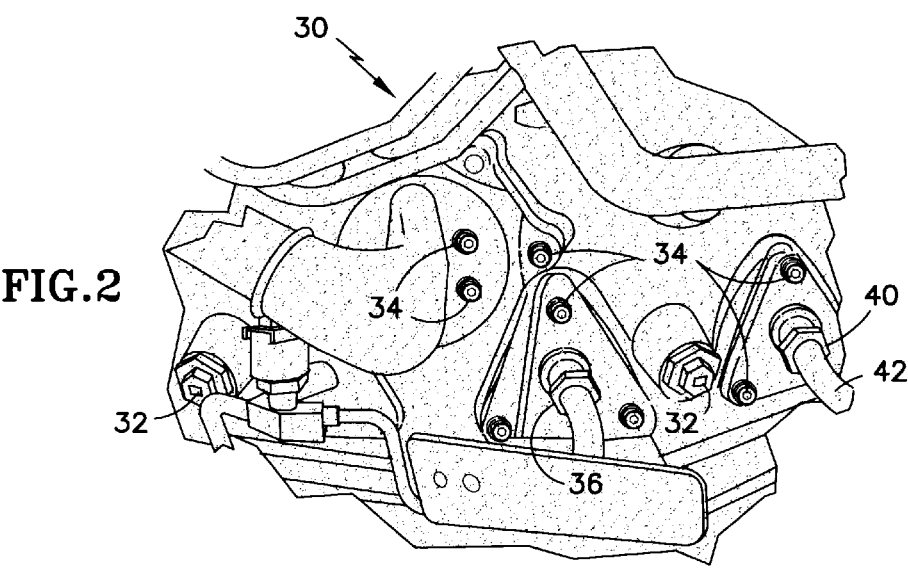
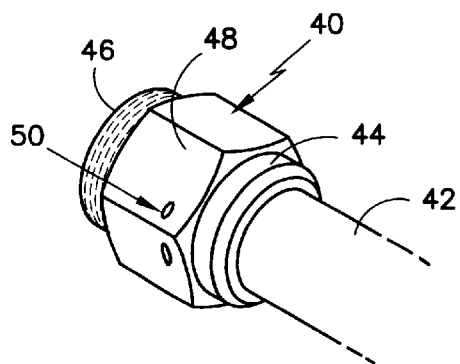
FIG.3

METHOD OF ASSEMBLY AND INSPECTION FOR A GAS TURBINE ENGINE

TECHNICAL FIELD

The invention relates to methods for assembly and inspection of a gas turbine engine and more particularly to methods for assembly and inspection of supplemental restraining devices, e.g., lock-wires, on components of a gas turbine engine.

BACKGROUND ART

A gas turbine engine has various components, e.g., fasteners, plugs, etc., that unless restrained can loosen and disengage due to vibration. Consequently, it has for many decades been a standard practice in the engine industry to install a supplemental restraining device such as lock-wire to prevent such components from loosening. There are various types of lock-wire, including but not limited to types referred to as safety wire and Bergen cable.

Even though lock-wire has been used for many decades, the installation of lock-wires remains time consuming and difficult. A single engine may have hundreds or thousands of components that require lock-wire. To avoid having the lock-wires cause obstruction or injury during assembly of the engine, the lock-wires are installed after the components have been attached to the engine. A mechanic uses a manual to determine the part numbers and the locations of the components that require lock-wire. The mechanic must then locate the components and install the lock-wires. However, most of the components on the engine are metallic or gray in color and thus visually blend together, thereby making it difficult to locate the components that require lock-wire. Furthermore, a number of the components that require lock-wire are underneath the engine or behind other components and thus not readily visible.

The inspection of lock-wires is also time consuming and difficult. Inspections are traditionally performed to determine whether lock-wires are installed on all of the components requiring one. However, in the course of the inspection, the inspector must locate each component that requires lock-wire using the same procedure as that used by the mechanic who installs the lock-wires.

DISCLOSURE OF THE INVENTION

An object of the present invention is to aid installation and inspection of supplemental restraining devices, e.g., lock-wires, by reducing the difficulty associated with locating the components that require supplemental restraining devices.

The present invention is predicated in part on the recognition that the time and the difficulty associated with locating components that require supplemental restraining devices can be reduced by increasing the visibility of the components that require supplemental restraining devices and at the same time decreasing the visibility of the surrounding components that do not require supplemental restraining devices.

According to a first aspect of the present invention, a method of locating a component requiring a supplemental restraining device on a portion of a gas turbine engine includes applying a fluorescent material to the component, and irradiating the component and surrounding components on the portion of the gas turbine engine with electromagnetic radiation that causes the fluorescent material to emit visible light and thereby increase the visibility of the component, and in addition, the electromagnetic radiation causing a decrease in the visibility of any surrounding components that do not have a fluorescent material.

In accordance with one detailed aspect of the present invention, the supplemental restraining device is a lock-wire.

In accordance with another detailed aspect of the present invention, applying a fluorescent material includes applying a fluorescent dye coating.

In accordance with another detailed aspect of the present invention, the electromagnetic radiation is ultraviolet light generated by a black light.

In accordance with another detailed aspect of the present invention, ambient lighting around the portion of the gas turbine engine is maintained at least in part.

According to a second aspect of the present invention, a method of locating a component requiring a supplemental restraining device on a portion of a gas turbine engine includes applying a fluorescent material to the component, and irradiating the component and surrounding components on the portion of the gas turbine engine with ultraviolet light that causes the fluorescent material to emit visible light and thereby increase the visibility of the component relative to any surrounding components that do not have a fluorescent material.

According to a third aspect of the present invention, a method of assembly includes locating a component that is to receive a lock-wire and installing a lock-wire that in the presence of the electromagnetic radiation has a visibly contrasting appearance compared to that of the component requiring a lock-wire.

According to a fourth aspect of the present invention a method of inspecting includes locating a component that requires a lock-wire, irradiating with the electromagnetic radiation, and inspecting for the presence of a visibly contrasting appearance.

A primary advantage of the present invention is a reduction in the difficulty associated with locating the components that require supplemental restraining devices on gas turbine engines, thereby aiding installation and inspection of the supplemental restraining devices.

These and other objects, features and advantages of the present invention will become more apparent in the light of the following detailed description, accompanying drawing, and claims.

BRIEF DESCRIPTION OF THE DRAWINGS

FIG. 1 is a perspective view of a gas turbine aircraft engine and a fuel manifold thereof;

FIG. 2 is a perspective view of a portion of the fuel manifold of FIG. 1 in an assembly stage;

FIG. 3 is a perspective view of a threaded, collared nut used to retain a fuel line to the fuel manifold of FIG. 1;

BEST MODE EMBODIMENT FOR CARRYING OUT THE INVENTION

Figure 4:
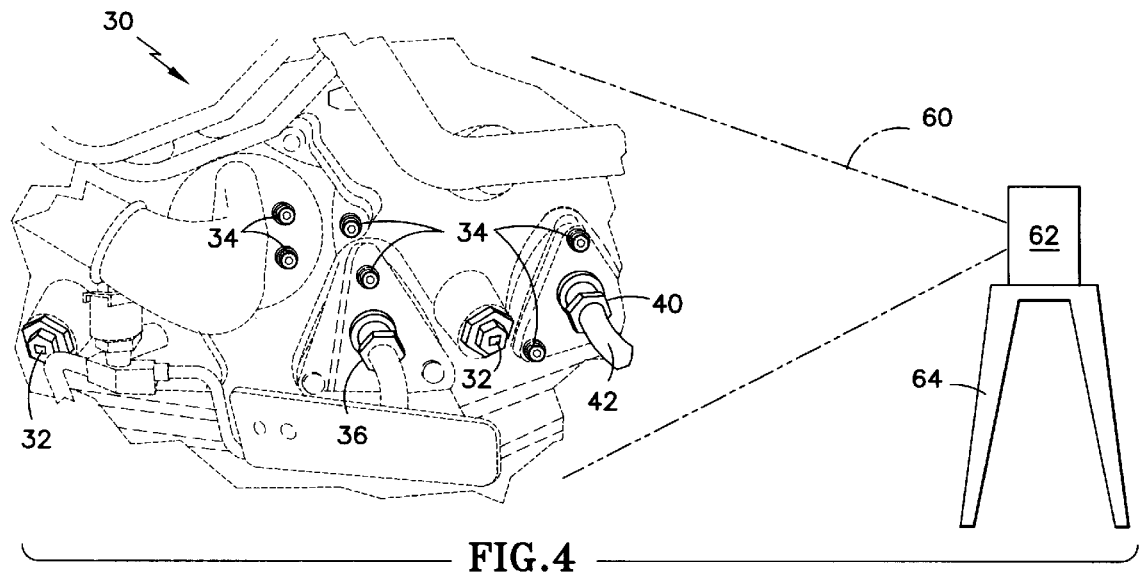
FIG. 4 is a perspective view of a portion of the fuel manifold of FIG. 1 showing components that require lock-wire and have a fluorescent dye coating as well as surrounding components that do not require lock-wire and do not have a fluorescent dye coating, and an electromagnetic radiation source that generates electromagnetic radiation to excite the fluorescent dye in the coatings.

The present invention is disclosed herein with respect to an embodiment for use in installing and inspecting lock-wires on fasteners used on a fuel manifold of a gas turbine engine 20 represented in FIG. 1.

FIG. 1 is a side elevation view of a gas turbine engine 20 for powering an aircraft. The engine 20 includes a compressor section 24, a combustor section 26, and a turbine section 28. The combustor section 26 has a fuel manifold 30.

Referring now to FIG. 2, in an illustration of a portion of the fuel manifold 30 during an assembly stage, the fuel manifold 30 has a plurality of components. Some of the plurality of components require but do not yet have lock-wire installed. The components that require lock-wire are of various types including plugs 32, and fasteners (e.g., bolts 34 and nuts 36). One of the components requiring lock-wire is a nut 40 that retains a fuel line 42 to the fuel manifold 30.

Referring now to FIG. 3, in a view of the nut 40 and the fuel line 42 detached from the fuel manifold 30, the nut 40 has one end 44 with a collar and one threaded end 46. The end 44 engages the fuel line 42, the threaded end 46 (threads shown in phantom) engages the fuel manifold 30. The nut 40 further has a surface 48 and a hole 50 that extends from one part of the surface to another part of the surface. The hole 50 is to adapted to receive a lock-wire.

Referring again to FIG. 2, the components that require lock-wire must be located on the fuel manifold 30 in order to install the lock-wires. However, most of the components on the fuel manifold 30 are metallic or gray in color and thus visually blend together, thereby making it difficult to locate some or all of the components that require lock-wire.

To assist in locating the components that require lock-wire, each of such components comprises a fluorescent material preferably in the form of a coating on the surface of the component. The coating comprises a fluorescent dye and is applied in any suitable manner including but not limited to brushing, spraying, dipping, forming, and combinations thereof. The coating is preferably applied prior to assembling the component to the fuel manifold 30. The fluorescent dye may have any suitable color including but not limited to fluorescent green. Fluorescent dyes are typically barely visible in daylight and the ambient light of the assembly area. Note that the ambient light in the assembly area is typical of that found in gas turbine engine assembly areas.

Referring now to FIG. 4, at least a portion of the portion of the fuel manifold 30 is irradiated with electromagnetic radiation 60. The ambient lighting in the assembly area is preferably maintained, at least in part, so as not to result in a safety hazard around the engine. If an irradiated component has a fluorescent dye coating, the electromagnetic radiation excites the fluorescent dye in the coating, resulting in a fluorescent emission from the coating. The fluorescent emission increases the visibility of these component 32, 34, 36, 40 and increases the visibility of these components relative to any surrounding components that do not have a fluorescent material. In addition, while one might expect the visibility of an irradiated component to remain constant (for a given ambient lighting condition) if the component does not have a fluorescent coating, it has been found that the visibility of such a component actually decreases upon irradiating with the electromagnetic radiation. Although not exactly understood, the decrease in the visibility of the components that do not have a fluorescent coating may be a consequence of the manner in which the human eye responds to the increase in the visibility of the components that do have a fluorescent dye coating. This decrease in visibility in combination with the increase in the visibility of the components with fluorescent dye coatings cause the components that require lock-wire 32, 34, 36, 40 to visibly "stand out" in a dramatic way, compared to any surrounding components that do not have a fluorescent material, thereby aiding in the location of the components that require lock-wire 32, 34, 36, 40.

The electromagnetic radiation 60 may be generated by any suitable electromagnetic radiation source 62 including but not limited to a black light that produces ultraviolet light. The electromagnetic radiation source 62 may be hand held or mounted on a stand 64. The stand 64 may be a stationary stand or a portable one. The electromagnetic radiation source 62 may have any suitable power and may be located it any suitable distance from the portion of the fuel manifold 30. In some embodiments, the fuel manifold 30 is moved to a dedicated area outfitted with at least one electromagnetic radiation source.

Figure 5:
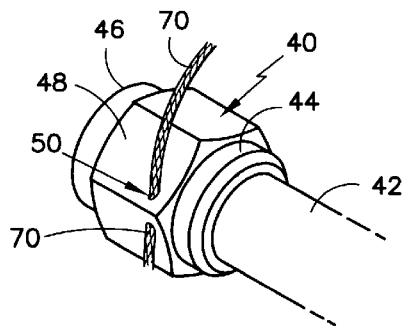
FIG. 5 is a perspective view of the nut of FIG. 3 and a lock-wire installed in the nut.

Referring now to FIG. 5, after a component requiring lock-wire, e.g., the nut 40, is located, a lock-wire 70 is installed. Although this step may be performed while irradiating with the electromagnetic radiation, it may alternatively be performed without the irradiation if normal visibility is desired. The lock-wire 70 further attaches to at least one other component on the manifold 30 to prevent the component requiring lock-wire, e.g., the nut 40, from loosening due to vibration.

An inspection is subsequently performed to verify that a lock-wire is properly installed on each component that requires one. Components requiring lock-wire may be located in the same manner as that described above with respect to locating components prior to installation of the lock-wires. Note that the ambient lighting in the area is preferably maintained, at least in part, so as not to result in a safety hazard around the engine.

After locating a component that requires a lock-wire, the component is inspected to confirm that a lock-wire is properly installed. Although this step may be performed while irradiating with the electromagnetic radiation, it may alternatively be performed without the irradiation if normal visibility is desired. A flashlight (not shown) may be used to produce additional visible light if needed.

Figure 6:
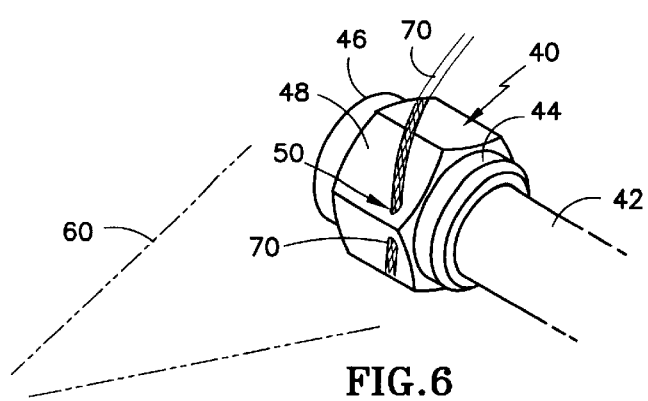
FIG. 6 is a perspective view of the nut and lock-wire of FIG. 3 during irradiation by the electromagnetic radiation of FIG. 4.

Referring now to FIG. 6, the above step may be performed while irradiating with the electromagnetic radiation 60 as follows. The electromagnetic radiation 60 causes the coating to produce a fluorescent emission. If a lock-wire is installed, the lock-wire 70 has a portion 72 having a visibly contrasting appearance on the nut 40, and at least a portion of the lock-wire 70 is within the hole 50 of the component such that the portion is visibly obscured to some degree. Thus, the presence of the visibly contrasting appearance and the obscured portion of the lock-wire indicates that a lock-wire is installed. Alternatively, an absence of the contrasting appearance or the obscured portion of the lock-wire indicates that a lock-wire is not installed.

In some embodiments, the lock-wire comprises a fluorescent material preferably in the form of a fluorescent dye coating. The fluorescent dye in the coating applied to the lock-wire may contrast with the color of the fluorescent dye in the coatings of the components requiring lock-wire. In the latter case, if the components requiring lock-wire have a green colored fluorescent dye, the coating for the lock-wire may for example have an orange colored fluorescent dye.

While disclosed with reference to embodiments for locating components that require lock-wire, the present invention may be used to identify components that require any type of supplemental restraining device to prevent the component from loosening including but not limited to lock-wire, nuts, bolts, screws, pins, pegs, and springs.

The present invention may be used to locate components on any portion of the engine. The portion may be of any size and may or may not be part of a fully assembled engine at the time.

Although the present invention has been described with reference to a best mode embodiment, this description is not meant to be construed in a limiting sense. Various modifications of the best mode embodiment, as well as additional embodiments of the invention, will be apparent to persons skilled in the art upon reference to this description, without departing from the spirit of the invention, as recited in the claims appended hereto. It is therefore contemplated that the appended claims will cover any such modifications or embodiments as fall within the true scope of the invention.

What is claimed is:

1. A method of locating a component requiring a supplemental restraining device on a portion of a gas turbine engine, the method comprising the steps of:

applying a fluorescent material to the component; and irradiating the portion of the gas turbine engine with an electromagnetic radiation that causes the fluorescent material on the component to emit visible light and thereby increase the visibility of the component, the electromagnetic radiation further causing a decrease in the visibility of any surrounding components that do not have a fluorescent material.

2. The method of claim 1 wherein the supplemental restraining device is a lock-wire.

3. The method of claim 2 wherein the step of applying a fluorescent material comprises the step of applying a coating having a fluorescent dye.

4. The method of claim 3 wherein the electromagnetic radiation is ultraviolet light generated by a black light and the ambient lighting around the portion of the gas turbine engine is maintained at least in part.

5. The method of claim 2 wherein the electromagnetic radiation is ultraviolet light generated by a black light.

6. The method of claim 2 wherein the ambient lighting around the portion of the gas turbine engine is maintained at least in part.

7. The method of claim 1 wherein the step of applying a fluorescent material comprises the step of applying a coating having a fluorescent dye.

8. The method of claim 1 wherein the electromagnetic radiation is ultraviolet light generated by a black light.

9. The method of claim 1 wherein ambient lighting around the portion of the gas turbine engine is maintained at least in part.

10. A method of assembly comprising the steps of claim 1 and further comprising the step of installing a lock-wire that in the presence of the electromagnetic radiation has a visibly contrasting appearance compared to that of the component requiring a lock-wire.

11. The method of claim 10 wherein the lock-wire does not have a coating with a fluorescent dye.

12. The method of claim 10 wherein the lock-wire has a coating with a fluorescent dye.

13. A method for use in inspecting a portion of a gas turbine engine, the method comprising the steps of claim 1 wherein the component requiring a lock-wire has a hole and the lock-wire is inserted into the hole, and further comprising the step of:

irradiating with the electromagnetic radiation;

and inspecting for the presence of a visibly contrasting appearance on the component requiring a lock-wire.

14. The method of claim 13 wherein the step of inspecting further includes inspecting for the presence of a visibly obscured portion of the lock-wire.

15. A method of locating a component requiring a supplemental restraining device on a portion of a gas turbine engine, the method comprising the steps of:

applying a fluorescent material to the component; and irradiating the portion of the gas turbine engine with ultraviolet light that causes the fluorescent material on the component to emit visible light and thereby causes an increase in the visibility of the component relative to any surrounding components that do not have a fluorescent material.

16. The method of claim 15 wherein the supplemental restraining device is a lock-wire.

17. The method of claim 16 wherein the step of applying a fluorescent material comprises the step of applying a coating having a fluorescent dye, the ultraviolet light is generated by a black light, and the ambient lighting around the portion of the gas turbine engine is maintained at least in part.

18. The method of claim 15 wherein the step of applying a fluorescent material comprises the step of applying a coating having a fluorescent dye.

19. The method of claim 15 wherein the ultraviolet light is generated by a black light.

20. The method of claim 15 wherein ambient lighting around the portion of the gas turbine engine is maintained at least in part.

* * * * *